(12) United States Patent
Ida

(10) Patent No.: US 9,814,440 B2
(45) Date of Patent: Nov. 14, 2017

(54) MEASUREMENT APPARATUS AND A METHOD FOR TEMPERATURE DEPENDENT FREQUENCY CHANGE MEASUREMENT IN A BODY PART VIA ULTRASONIC MEASUREMENTS

(71) Applicant: ADVANTEST CORPORATION, Tokyo (JP)

(72) Inventor: Taiichiro Ida, Gunma (JP)

(73) Assignee: ADVANTEST CORPORATION, Tokyo (JP)

( * ) Notice: Subject to any disclaimer, the term of this patent is extended or adjusted under 35 U.S.C. 154(b) by 232 days.

(21) Appl. No.: 14/621,391

(22) Filed: Feb. 13, 2015

(65) Prior Publication Data

US 2015/0272539 A1 Oct. 1, 2015

(30) Foreign Application Priority Data

Mar. 25, 2014 (JP) .................................. 2014-062181

(51) Int. Cl.
 *A61B 8/08* (2006.01)
 *A61B 5/00* (2006.01)
(52) U.S. Cl.
 CPC .............. *A61B 8/08* (2013.01); *A61B 5/4244* (2013.01); *A61B 5/4872* (2013.01); *A61B 8/5223* (2013.01)

(58) Field of Classification Search
 CPC ........ A61B 8/08; A61B 5/4244; A61B 5/4872
 See application file for complete search history.

(56) References Cited

U.S. PATENT DOCUMENTS

| 3,948,248 A | * | 4/1976 | Zuckerman | ............ A61B 3/165 |
| | | | | 367/94 |
| 2003/0144592 A1 | * | 7/2003 | Jeong | ........................ A61B 8/08 |
| | | | | 600/438 |
| 2006/0020205 A1 | * | 1/2006 | Kamiyama | ............ A61B 8/469 |
| | | | | 600/437 |
| 2013/0018262 A1 | | 1/2013 | Matsunaka et al. | |

FOREIGN PATENT DOCUMENTS

WO 2011/125549 A1 10/2011

\* cited by examiner

*Primary Examiner* — Serkan Akar

(57) ABSTRACT

To measure the content percentage of fat in a liver without increasing hardware size, provided is a measurement apparatus that supplies an ultrasonic signal to a body part and receives a response signal that has passed through an inner portion of the body part, the measurement apparatus including an ultrasonic signal generating section that generates the ultrasonic signal according to a control signal; a loop control section that supplies the control signal to the ultrasonic signal generating section in response to receiving the response signal that has passed through the body part; and a frequency measuring section that measures a repeating frequency of the control signal repeatedly supplied by the loop control section.

6 Claims, 3 Drawing Sheets

MEASUREMENT APPARATUS AND A METHOD FOR TEMPERATURE DEPENDENT FREQUENCY CHANGE MEASUREMENT IN A BODY PART VIA ULTRASONIC MEASUREMENTS

The contents of the following Japanese patent application(s) are incorporated herein by reference: 2014-062181 filed in JP on Mar. 25, 2014.

BACKGROUND

1. Technical Field

The present invention relates to a measurement apparatus, a measurement method, and an ultrasonic measurement apparatus.

2. Related Art

It is known that the speed of sound passing through physical matter changes according to temperature and that the amount of this change differs according to the type of physical matter. For example, it is known that the speed of sound when propagating through muscle or internal organs, which contain a large amount of water, and the speed of sound propagating through fat cells experience different changes in speed in response to changes in temperature. Therefore, it is known that by applying ultrasonic waves to the liver or the like and measuring the change in speed of a reflected ultrasonic signal in response to a change in temperature of the liver, the liver can be diagnosed as being a fatty liver or not, as shown in International Publication WO 2011/125549, for example.

However, the change in speed of the ultrasonic wave that is dependent on the physical matter in this way is indicated by only a slight difference between approximately +2 m/s·° C. in water and approximately −4 m/s·° C. in fat cells, and therefore the received ultrasonic reflected signal must be processed through an A/D conversion with a high speed sampling rate of at least several hundred MHz. Furthermore, when the measurement point fluctuates due to breathing or the like during measurement, there is an error in the measurement results, and therefore signal processing such as calculating the correlation of a plurality of pieces of data is necessary, which increases the physical dimensions of the measurement apparatus.

SUMMARY

Therefore, it is an object of an aspect of the innovations herein to provide a measurement apparatus, a measurement method, and an ultrasonic measurement apparatus, which are capable of overcoming the above drawbacks accompanying the related art. The above and other objects can be achieved by combinations described in the claims. According to first aspect of the invention, provided is a measurement apparatus that supplies an ultrasonic signal to a body part and receives a response signal that has passed through an inner portion of the body part, the measurement apparatus comprising an ultrasonic signal generating section that generates the ultrasonic signal according to a control signal; a loop control section that supplies the control signal to the ultrasonic signal generating section in response to receiving the response signal that has passed through the body part; and a frequency measuring section that measures a repeating frequency of the control signal repeatedly supplied by the loop control section.

According to second aspect of the invention, provided is an ultrasonic measurement apparatus comprising the measurement apparatus according to the first aspect and a temperature adjusting section that changes a temperature of the inner portion of the body part.

The summary clause does not necessarily describe all necessary features of the embodiments of the present invention. The present invention may also be a sub-combination of the features described above

DESCRIPTION OF EXEMPLARY EMBODIMENTS

Hereinafter, some embodiments of the present invention will be described. The embodiments do not limit the invention according to the claims, and all the combinations of the features described in the embodiments are not necessarily essential to means provided by aspects of the invention.

Figure 1:
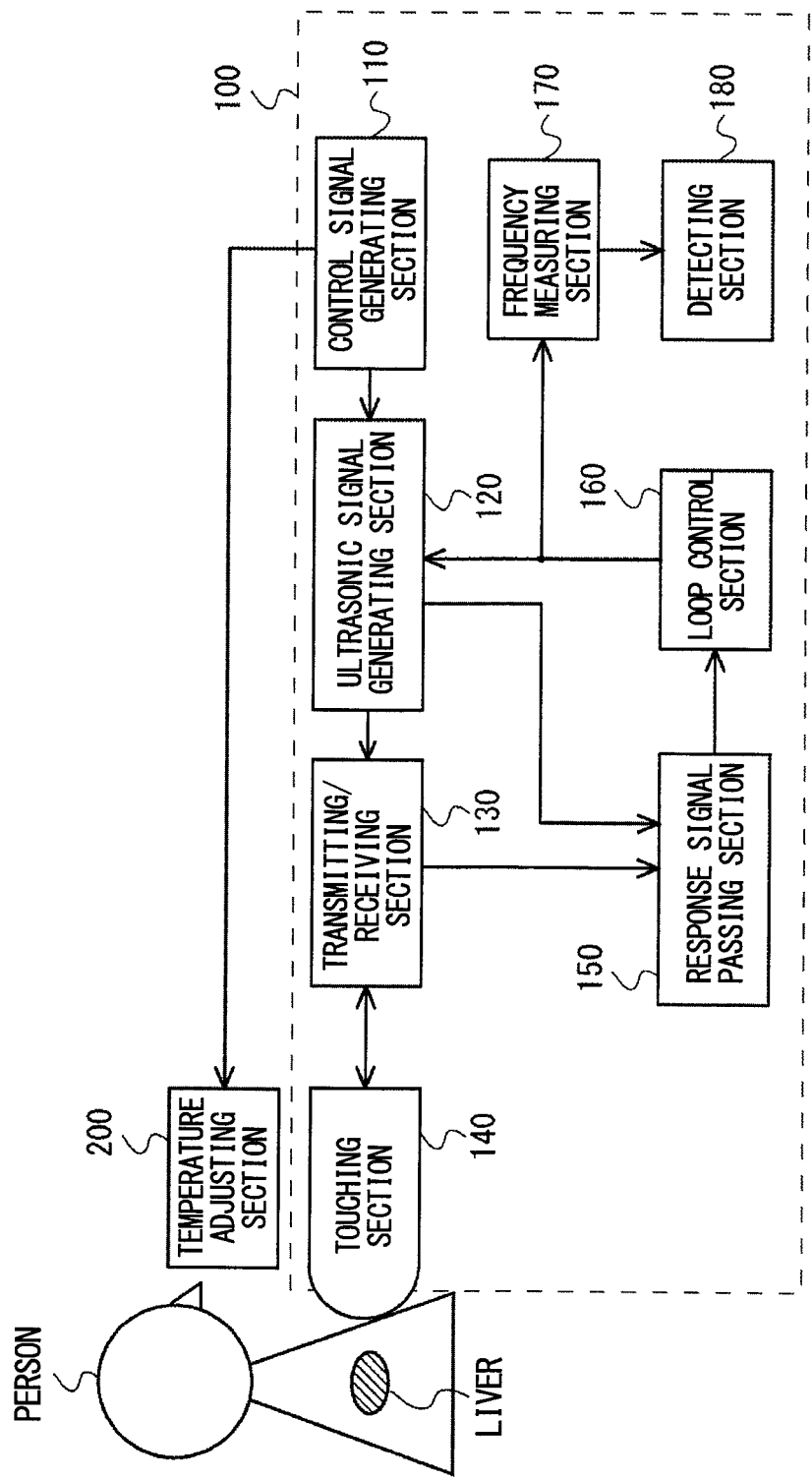
FIG. 1 shows an exemplary configuration of a measurement apparatus 100 according to an embodiment of the present invention, along with a temperature adjusting section 200.

FIG. 1 shows an exemplary configuration of a measurement apparatus 100 according to an embodiment of the present invention, along with a temperature adjusting section 200. The measurement apparatus 100 supplies an ultrasonic signal to a part of a body and receives a response signal that has passed through an inner portion of this part of the body. The measurement apparatus 100 detects the physical matter contained in the body part according to a change in the speed of the response signal, by measuring the looping frequency at which the response signal travels around a loop path.

The measurement apparatus 100 may detect the physical matter contained in a body part of an animal, particularly the physical matter contained in a body part of a human. The measurement apparatus 100 preferably has, as the body part serving as the measurement target, organs or tissue that contain homogenous physical matter. The present embodiment describes an example in which the measurement apparatus 100 uses a liver as the body part to be the measurement target.

The measurement apparatus 100 irradiates the liver of a person with an ultrasonic signal, and may receive, as a response signal, an ultrasonic signal that has passed through the liver. For example, the measurement apparatus 100 receives a reflected signal that has been reflected from of the inner portion of the liver as the response signal. FIG. 1 shows an example in which the measurement apparatus 100 receives a reflected signal generated at a border between lobes of the liver, e.g. the right lobe, the left lobe, the caudate lobe, and the quadrate lobe, as the response signal. Furthermore, the temperature of the inner portion of the body part is changed by the temperature adjusting section 200, and the measurement apparatus 100 detects the change in speed of the received signal caused by the temperature change of the inner portion of the liver.

The temperature adjusting section 200 may be provided outside of the measurement apparatus 100, or may instead be formed integrally as a portion of the measurement apparatus 100. In this case, the measurement apparatus 100 and the temperature adjusting section 200 may together form an ultrasonic measurement apparatus. The temperature adjusting section 200 includes an irradiating section that irradiates the liver with ultrasonic or electromagnetic waves, for example, and changes the temperature of the inner portion of the liver. The temperature adjusting section 200 may include a heating control section, for example, that controls the intensity and irradiation time, for example, of the radiated ultrasonic waves or the like such that the temperature of the inner portion of the liver changes to be a predetermined temperature.

The temperature adjusting section 200 may include a plurality of irradiating sections, and may perform irradiation by focusing ultrasonic waves or electromagnetic waves at a predetermined location in the inner portion of the liver. Instead, the temperature adjusting section 200 may include a cooling section that cools the inner portion of the liver. The temperature adjusting section 200 may touch the body of a person to supply the ultrasonic waves or the like.

The temperature adjusting section 200 stops irradiating the ultrasonic waves or electromagnetic waves after the temperature of the inner portion of the liver has risen, for example. Then, the measurement apparatus 100 supplies the ultrasonic signal until the raised temperature of the inner portion of the liver returns to the original temperature, and receives a response signal. The measurement apparatus 100 includes a control signal generating section 110, an ultrasonic signal generating section 120, a transmitting/receiving section 130, a touching section 140, a response signal passing section 150, a loop control section 160, a frequency measuring section 170, and a detecting section 180.

The control signal generating section 110 generates a control signal for generating the ultrasonic signal, and supplies this control signal to the ultrasonic signal generating section 120. If the measurement apparatus 100 includes a button for turning generation of the ultrasonic signal ON and OFF, the control signal generating section 110 generation of the control signal for generating the ultrasonic signal may be performed in response to this button being turned ON. Instead, the control signal generating section 110 may cause the ultrasonic signal to be constantly output while the power of the measurement apparatus 100 is ON.

The control signal generating section 110 is connected to the temperature adjusting section 200, and may supply the temperature adjusting section 200 with a control signal for changing the temperature of the inner portion of the liver. In this case, the control signal generating section 110 supplies the temperature adjusting section 200 with the control signal for changing the temperature of the inner portion of the liver and then, after a predetermined time has passed, supplies the ultrasonic signal generating section 120 with the control signal for generating the ultrasonic signal.

The ultrasonic signal generating section 120 is connected to the control signal generating section 110, and generates the ultrasonic signal according to the control signal received from the control signal generating section 110. The ultrasonic signal generating section 120 supplies the ultrasonic signal to the portion including the liver, through the transmitting/receiving section 130 and the touching section 140. The ultrasonic signal generating section 120 includes a puller for generating ultrasonic waves and outputs a high-voltage pulse in which the wave peak reaches from tens to a hundred and tens of volts, for example.

The transmitting/receiving section 130 is connected to the ultrasonic signal generating section 120 and the touching section 140, and supplies the ultrasonic signal received from the ultrasonic signal generating section 120 to the touching section 140. The transmitting/receiving section 130 is also connected to the response signal passing section 150, and supplies the response signal passing section 150 with the response signal received from the touching section 140. The transmitting/receiving section 130 includes a transmission/reception switch for the ultrasonic signal.

The touching section 140 touches the human body and supplies the liver of an inner portion of the human body with the ultrasonic signal generated by the ultrasonic signal generating section 120. The touching section 140 faces the measurement point or measurement region of the inner portion of the liver, contacts a location near the measurement point in the inner portion of the liver, and supplies the ultrasonic signal or the like such that the ultrasonic signal efficiently irradiates the measurement point or measurement region in the inner portion of the liver. Furthermore, the touching section 140 receives, as the response signal, the reflected signal generated from the measurement point or measurement region in the inner portion of the liver. The touching section 140 supplies the transmitting/receiving section 130 with the received response signal.

The response signal passing section 150 is provided between the ultrasonic signal generating section 120 and the loop control section 160, passes the response signal supplied from the touching section 140 to the loop control section 160, and attenuates the ultrasonic signal that leaks from the transmitting/receiving section 130. The response signal passing section 150 includes an amplification circuit with variable amplification and/or a switch circuit that amplify or attenuate a signal input thereto, according to a timing signal input thereto.

The response signal passing section 150 is connected to the ultrasonic signal generating section 120 and acquires the timing at which the ultrasonic signal is attenuated from the ultrasonic signal generating section 120, for example. Instead, the response signal passing section 150 may be connected to the control signal generating section 110 and may acquire the timing at which the ultrasonic signal is attenuated from the control signal generating section 110.

The loop control section 160 is connected to the ultrasonic signal generating section 120 and the response signal passing section 150, and supplies the ultrasonic signal generating section 120 with the control signal for generating the ultrasonic signal, in response to receiving the response signal from the liver from the response signal passing section 150. Specifically, the ultrasonic signal generating section 120, the transmitting/receiving section 130, the touching section 140, the liver, the response signal passing section 150, and the loop control section 160 form a loop path through which a signal based on the ultrasonic signal is sequentially transmitted.

The frequency measuring section 170 is connected to the loop control section 160 and measures the repeating frequency of the control signal that is repeatedly supplied to the ultrasonic signal generating section 120 by the loop control section 160 according to the response signal. The frequency measuring section 170 may be a frequency counter that counts how many times the electrical signal is input per unit time, to measure the frequency of this electrical signal. The frequency measuring section 170 supplies the detecting section 180 with the measured frequency.

The detecting section 180 is connected to the frequency measuring section 170 and detects the physical material contained in the liver through which the ultrasonic signal has passed, based on the frequency measured by the frequency measuring section 170. For example, the detecting section 180 detects a change in the frequency measured by the frequency measuring section 170, and detects the content percentage of fat in the liver.

The measurement apparatus 100 of the present embodiment described above does not need to be housed in a single case, and may be housed in a plurality of divided cases that are connected to each other by cables. Here, at least the case that houses the touching section 140 preferably has a size, shape, and weight that enable this case to be held in the hand of a user operating the measurement apparatus 100, i.e. the person performing the measurement, and is used to touch the body of the person undergoing the measurement.

The measurement apparatus 100 of the present embodiment described above forms a loop path that supplies the liver with an ultrasonic signal according to a received response signal, acquires speed information for the response signal by measuring the frequency of the signal traveling around the loop path, and detects the physical matter contained in the liver based on the change in speed of the response signal. The operation of the measurement apparatus 100 is described below using an operational flow chart.

Figure 2:
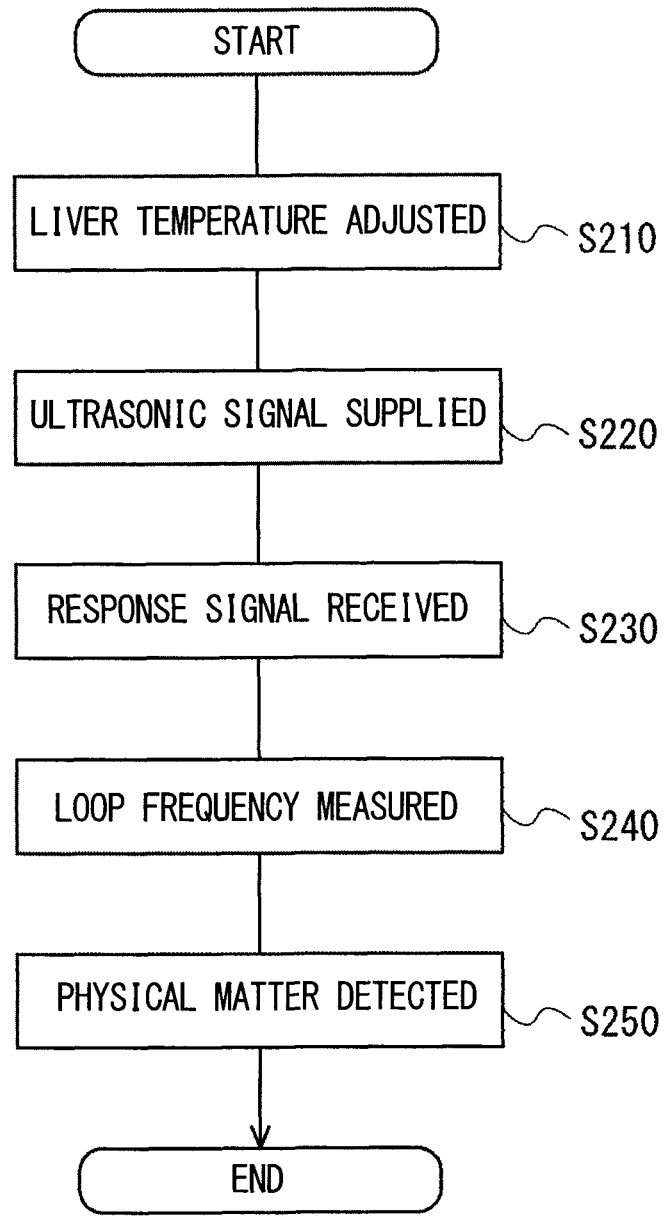
FIG. 2 shows an operational flow of the measurement apparatus 100 according to the present embodiment.

FIG. 2 shows an operational flow of the measurement apparatus 100 according to the present embodiment. The following describes an example in which the measurement apparatus 100 according to the present embodiment detects the content percentage of fat in the liver by performing steps S210 to S250 shown in FIG. 2.

First, the control signal generating section 110 supplies the temperature adjusting section 200 with the control signal for changing the temperature within the inside portion of the liver, to adjust the temperature within the inside portion of the liver before the liver is supplied with the ultrasonic signal from the ultrasonic signal generating section 120 (S210). For example, prior to supplying the ultrasonic signal, the control signal generating section 110 supplies a control signal for increasing the temperature of the inner portion the liver to a predetermined temperature. The temperature adjusting section 200 adjusts the temperature of the inner portion the liver to be the predetermined temperature, according to this control signal.

Next, the control signal generating section 110 supplies the ultrasonic signal generating section 120 with the control signal for generating the ultrasonic signal, and the ultrasonic signal is supplied to the inner portion of the liver (S220). The control signal generating section 110 raises the temperature of the inner portion of the liver to the predetermined temperature, and then supplies the ultrasonic signal generating section 120 with the control signal for generating the ultrasonic signal.

For example, the control signal generating section 110 supplies the control signal to the temperature adjusting section 200 and then, after a predetermined time has passed, supplies the ultrasonic signal generating section 120 with the control signal for generating the ultrasonic signal. In this case, the actual transition time needed for the temperature of the inner portion of the liver to change from when the temperature adjusting section 200 begins adjusting the temperature within the liver is measured in advance, and the time at which the ultrasonic signal generating section 120 supplies the control signal may be determined in advance according to the transition time measurement result. In this way, the measurement apparatus 100 can measure the temperature conditions from when the temperature of the liver is raised to the predetermined temperature to when the temperature of the liver has dropped back down to normal body temperature.

The ultrasonic signal generating section 120 supplies the ultrasonic signal to the inner portion of the liver through the transmitting/receiving section 130 and the touching section 140, according to the received control signal. Here, the ultrasonic signal generating section 120 may notify the response signal passing section 150 concerning the timing at which the ultrasonic signal is generated. The response signal passing section 150 acquires the timing at which the ultrasonic signal received from the ultrasonic signal generating section 120 is generated, as the timing at which the input signal is attenuated, and may attenuate the input signal from when this timing is acquired until a predetermined time has passed.

If there is an amplification circuit included, for example, the response signal passing section 150 decreases the amplification amount of the amplification circuit to attenuate the signal strength of the signal component supplied to the loop control section 160. Furthermore, if there is a switch circuit included, the response signal passing section 150 switches this switch circuit to cut off the electrical connection between the transmitting/receiving section 130 and the loop control section 160. In this way, the response signal passing section 150 attenuates the input signal in synchronization with the generation timing of the ultrasonic signal, even when a portion of the ultrasonic signal generated by the ultrasonic signal generating section 120 is leaked from the transmitting/receiving section 130 and input, and therefore the response signal passing section 150 can reduce the noise component and prevent incorrect operation of the loop control section 160.

Here, the response signal passing section 150 may determine in advance the time during which the input signal continues to be attenuated, according to the time during which the pulse is continuously generated as the ultrasonic signal by the ultrasonic signal generating section 120, and the attenuation of the input signal may be stopped after this predetermined time has passed. In this way, every time the ultrasonic signal generating section 120 generates the ultrasonic signal, the response signal passing section 150 can repeatedly switch whether the input signal is being attenuated, thereby reducing or blocking out the signal components other than the response signal.

Next, the touching section 140 receives the response signal, which is the reflected signal of the ultrasonic signal reflected from the inner portion of the liver (S230). The touching section 140 supplies the response signal passing section 150 with the received response signal through the transmitting/receiving section 130. The response signal passing section 150 passes the received response signal to the loop control section 160. Specifically, the response signal passing section 150 sets the amplification amount of the amplification circuit and/or the switches the switch circuit such that the response signal is passed to the loop control section 160.

For example, during periods other than the period in which a portion of the ultrasonic signal generated by the ultrasonic signal generating section 120 is leaked from the transmitting/receiving section 130 and input, the response signal passing section 150 passes the signal input thereto to the loop control section 160. Furthermore, the response signal passing section 150 may determine the timing at which the response signal is passed to the loop control section 160 according to the distance between the inner portion of the liver and the touching section 140 of the measurement apparatus 100.

The response signal to be passed to the loop control section 160 is the reflected signal that has been reflected from the inner portion of the liver, and therefore the timing at which the response signal is input to the response signal passing section 150 is determined according to the distance between the touching section 140 and the border between lobes in the inner portion of the liver, for example. Accordingly, the passage time corresponding to the distance that can be obtained between the touching section 140 and the inner portion of the liver is preferably obtained in advance based on information such as the position of the liver of the person and the position where the touching section 140 touches the person. The response signal passing section 150 may perform the setting of the amplification amount of the amplification circuit and/or the switching of the switch such that the response signal is passed during the passage time.

Instead of or in addition to the above, the response signal passing section 150 may pass a signal that exceeds a predetermined amplitude value and may attenuate a signal that is below this amplitude value. In this way, the loop control section 160 can reduce or cut off signals that have an amplitude value below the amplitude value that can be predicted for the response signal. Furthermore, when the amplitude value of a signal leaked from the transmitting/receiving section 130 and input, for example, is less than the predetermined amplitude value, the response signal passing section 150 need not perform the process to attenuate the input signal. If the response signal passing section 150 includes an amplification circuit, the response signal passing section 150 may amplify the signal to be passed, and then pass the resulting signal.

Next, upon receiving the response signal passed by the response signal passing section 150, the loop control section 160 supplies the control signal for generating the ultrasonic signal to the ultrasonic signal generating section 120. The ultrasonic signal generating section 120 generates the ultrasonic signal according to this control signal, and supplies the ultrasonic signal to the inner portion of the liver.

In the manner described above, the measurement apparatus 100 of the present embodiment supplies the ultrasonic signal to the liver in response to receiving the response signal that has passed through the liver, and therefore the supply of this ultrasonic signal and the reception of this response signal are repeated. Specifically, a signal based on the ultrasonic signal travels around the loop path formed by the ultrasonic signal generating section 120, the transmitting/receiving section 130, the touching section 140, the liver, the touching section 140, the response signal passing section 150, and the loop control section 160.

The frequency measuring section 170 measures the loop frequency at which the signal based on the ultrasonic signal travels around the loop path (S240). Specifically, the frequency measuring section 170 measures the speed of the signal passing through the loop path and the loop frequency determined according to the loop length, and therefore detects the frequency corresponding to the response speed. In other words, the speed information of the signal passing through the loop path can be acquired according to the frequency measured by the frequency measuring section 170. For example, when there is a difference in the speed at which the ultrasonic signal passes through different physical matter, the frequency measuring section 170 can detect the difference between these physical matter as the difference in the loop frequency.

As an example, the water, fat, and the like contained in the liver has an almost uniform distribution in the inner portion of the liver, and therefore the speed of the ultrasonic wave passing through the liver depends on the amount of water, fat, and the like contained in the liver. Accordingly, a liver in which the content percentage of water is low enough and the content percentage of fat is high enough to create a difference in speed when compared to a normal liver can be detected due to the difference in the loop frequency.

Furthermore, even when the content percentage of the physical material or between physical materials is such that it is difficult to detect this difference as the difference in the loop frequency, there are cases where this difference can still be detected by utilizing the temperature dependent nature of the loop frequency. For example, the temperature dependency of the speed of an ultrasonic wave is approximately +2 m/s·° C. in water and approximately −4 m/s·° C. in fat cells, thereby exhibiting different directions of change in the speed relative to temperature. Accordingly, in the case of a liver containing a greater amount of water, the loop frequency decreases when the temperature decreases, while in the case of a liver containing a greater amount of fat, the loop frequency increases when the temperature decreases, and therefore the frequency measuring section 170 outputs the increase or decrease in the frequency corresponding to the content percentage of such physical matter.

The detecting section 180 detects the physical matter contained in the liver based on the change in frequency corresponding to the change in temperature in the inner portion of the liver (S250). Furthermore, the detecting section 180 may detect the content percentage of fat in the liver based on the slope of the change in frequency corresponding to the temperature change. For example, when the temperature dependency has a positive sign when the ultrasonic wave speed decreases, in response to there being a decrease in the loop frequency when the temperature decreases, the detecting section 180 detects that the content percentage of water in the liver is high. Here, by measuring in advance the speed change corresponding to the content percentage of fat in the liver and comparing this to the measurement results, the detecting section 180 may identify the content percentage of fat in the liver of the measurement target.

In the manner described above, the measurement apparatus 100 of the present embodiment acquires speed information for the ultrasonic signal passing through the inner portion of the liver by measuring the frequency of the signal travelling around the loop path. Accordingly, the measurement apparatus 100 can detect the speed of the response signal and changes in the speed without performing an A/D conversion with a high-speed sampling rate.

Furthermore, the frequency measuring section 170 can measure the loop frequency using a frequency counter. The frequency counter can improve the accuracy of the measured frequency by using a liquid crystal oscillator or the like to improve the time accuracy, and therefore the accuracy of the detected speed can be increased regardless of the sampling rate.

The frequency counter can easily perform measurement for a high frequency that exceeds 100 MHz, for example, by using a prescaler (frequency divider) to divide the input frequency and then measuring the frequency. Accordingly, the measurement apparatus 100 can improve the design freedom of the loop length. In this way, the measurement apparatus 100 can accurately measure the change in speed of the response signal, and can more accurately detect the content percentage of water or fat contained in the liver of the measurement target.

Furthermore, the frequency counter counts the pulses input per unit time, and can therefore finish the frequency measurement within this unit of time. Accordingly, even when a person is breathing, the frequency measuring section 170 can perform the frequency measurement faster than the person breaths, and can therefore reduce the effect of breathing on the measurement results. Furthermore, the frequency measuring section 170 can perform more frequency measurements during a period when the temperature of the liver drops back to normal body temperature after being increased to a predetermined temperature, and can therefore measure the change in frequency relative to change in temperature with a higher (temperature) resolution.

Yet further, by periodically measuring the liver of the person being targeted, the measurement apparatus 100 can detect the fat content percentage of the liver increasing or decreasing in response to the lifestyle of the person being measured, for example. The detecting section 180 may also have a simple diagnosis function to identify a liver as a fatty liver when the fat content of the liver is greater than or equal to a predetermined value. In the manner described above, the measurement apparatus 100 of the present embodiment can easily detect the physical matter contained in a liver without increasing the size of the apparatus by using high-speed digital signal processing.

Figure 3:
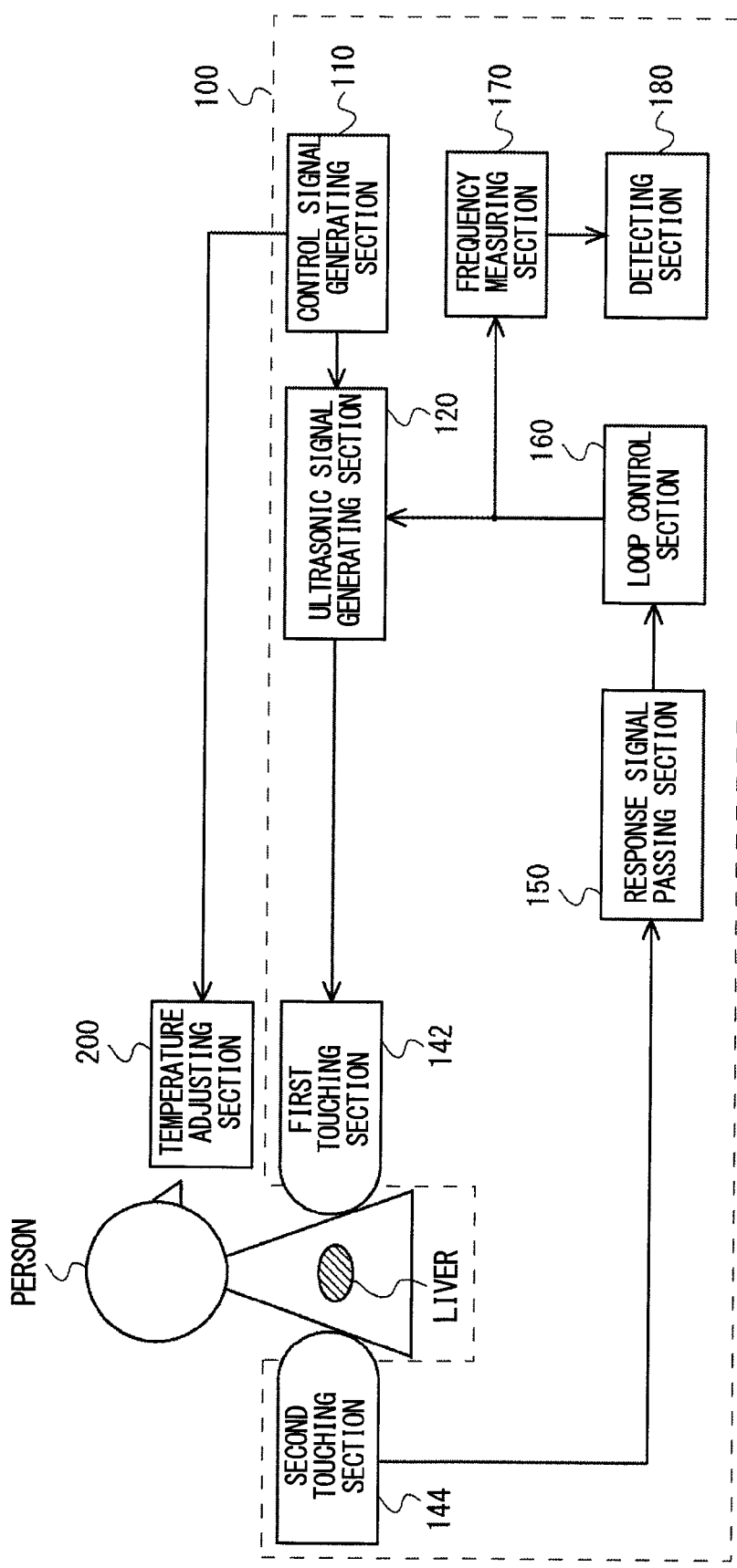
FIG. 3 shows a modification of the measurement apparatus 100 according to the present embodiment, along with the temperature adjusting section 200.

FIG. 3 shows a modification of the measurement apparatus 100 according to the present embodiment, along with the temperature adjusting section 200. In the measurement apparatus 100 of the present modification, components having substantially the same operation as components in the measurement apparatus 100 according to the embodiment shown in FIG. 1 are given the same reference numerals, and redundant descriptions are omitted. The measurement apparatus 100 of the present modification includes a first touching section 142 and a second touching section 144.

The first touching section 142 touches a human body and supplies the liver of the inner portion of the person with an ultrasonic signal generated by the ultrasonic signal generating section 120. In other words, the first touching section 142 includes at least the function of supplying the liver of the inner portion the person with an ultrasonic signal, which is a function of the touching section 140 according to the embodiment shown in FIG. 1.

The second touching section 144 touches the human body and receives the ultrasonic signal that has passed through the inner portion of the liver as a response signal. In other words, the second touching section 144 includes at least the function of receiving the response signal, which is a function of the touching section 140 according to the embodiment shown in FIG. 1.

The second touching section 144 supplies the loop control section 160 with the response signal, through the response signal passing section 150. The loop control section 160 causes the ultrasonic signal to be generated from the ultrasonic signal generating section 120 according to the response signal, and supplies the generated ultrasonic signal to the first touching section 142. In this way, the measurement apparatus 100 of the present modification creates a loop path formed by the ultrasonic signal generating section 120, the transmitting/receiving section 130, the first touching section 142, the liver, the second touching section 144, the response signal passing section 150, and the loop control section 160.

As a result, the second touching section 144 can receive the response signal based on the ultrasonic signal supplied from the first touching section 142 to the liver, from a location differing from the location where the first touching section 142 touches the human body. Therefore, the touching sections can be designed as separate and independent components on the transmission side and the reception side, thereby increasing the design freedom. Furthermore, a portion of the ultrasonic signal supplied from the first touching section 142 on the transmission side is prevented from leaking to the second touching section 144 on the reception side. Yet further, by optimizing the location at which each touching section touches the body, an ultrasonic signal that has passed through organs and tissue from the first touching section 142 can be received by the second touching section 144.

In the manner described above, the measurement apparatus 100 of the present modification divides the touching section 140 that touches the body into the first touching section 142 on the transmission side and the second touching section 144 on the reception side, to transmit and receive the ultrasonic signal. In this case as well, the measurement apparatus 100 can cause the signal based on the ultrasonic signal to travel around the loop path, acquire the speed information indicating the speed at which the ultrasonic signal travels through the liver or the like, and detect the physical matter included in the liver.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

What is claimed is:

1. A measurement apparatus comprising:
    an ultrasonic signal generator that generates an ultrasonic signal according to a control signal and supplies the ultrasonic signal to a body part;
    a loop controller that supplies the control signal to the ultrasonic signal generator in response to receiving a response signal that has passed through the body part;
    a frequency counter that measures a repeating frequency of the control signal repeatedly supplied by the loop controller; and
    a processor configured to detect change in the frequency measured by the frequency counter;
    wherein
    the ultrasonic signal generator supplies the ultrasonic signal to a portion containing a liver, which is the body part,
    the ultrasonic signal generator, the body part, and the loop controller form a loop path through which a signal based on the ultrasonic signal is sequentially transferred,
    the frequency counter measures a loop frequency at which the signal travels around the loop path, and
    the processor is further configured to
    detect physical matter contained in the body part based on the detected change in the frequency,
    detect a content percentage of fat in the liver based on a result of the detection, detect the physical matter contained in the body part based on change in the frequency corresponding to temperature change of the inner portion of the body part and detect the content percentage of fat in the body part based on a slope of the change in the frequency corresponding to the temperature change.

2. The measurement apparatus according to claim 1, wherein the processor is further configured to identify the liver as a fatty liver when the content percentage of fat in the liver is greater than or equal to a predetermined value.

3. The measurement apparatus according to claim 1, comprising:

a response signal passing section that is provided between the ultrasonic signal generator and the loop controller, and includes an amplification circuit that amplifies or attenuates a signal input thereto.

4. The measurement apparatus according to claim 1, wherein the response signal is a reflected signal that has been reflected from the inner portion of the body part.

5. A measurement apparatus comprising:

an ultrasonic signal generator that generates an ultrasonic signal according to a control signal and supplies the ultrasonic signal to a body part;

a loop controller that supplies the control signal to the ultrasonic signal generator in response to receiving a response signal that has passed through the body part;

a frequency counter that measures a repeating frequency of the control signal repeatedly supplied by the loop controller;

a processor configured to detect change in the frequency measured by the frequency counter; and a response signal passing section that is provided between the ultrasonic signal generator and the loop controller, passes the response signal to the loop controller, and attenuates the ultrasonic signal, wherein the ultrasonic signal generator, the body part, and the loop controller form a loop path through which a signal based on the ultrasonic signal is sequentially transferred, the frequency counter measures a loop frequency at which the signal travels around the loop path, the processor is further configured to detect physical matter contained in the body part based on the detected change in the frequency, and the response signal passing section acquires a timing at which the ultrasonic signal from the ultrasonic signal generator is attenuated.

6. A measurement apparatus comprising:

an ultrasonic signal generator that generates an ultrasonic signal according to a control signal and supplies the ultrasonic signal to a body part;

a loop controller that supplies the control signal to the ultrasonic signal generator in response to receiving a response signal that has passed through the body part;

a frequency counter that measures a repeating frequency of the control signal repeatedly supplied by the loop controller;

a processor configured to detect change in the frequency measured by the frequency counter; and a response signal passing section that is provided between the ultrasonic signal generator and the loop controller, passes the response signal to the loop controller, and attenuates the ultrasonic signal, wherein the ultrasonic signal generator, the body part, and the loop controller form a loop path through which a signal based on the ultrasonic signal is sequentially transferred, the frequency counter measures a loop frequency at which the signal travels around the loop path, the processor is further configured to detect physical matter contained in the body part based on the detected change in the frequency, and the response signal passing section determines a timing at which the response signal is passed to the loop controller, according to a distance between the measurement apparatus and the inner portion of the body part.

* * * * *